United States Patent [19]
Andersen et al.

[11] Patent Number: 5,840,081
[45] Date of Patent: Nov. 24, 1998

[54] SYSTEM AND METHOD FOR IMPLANTING CARDIAC VALVES

[76] Inventors: Henning Rud Andersen, Dalvangen 37A, DK-8270 Hoejbjerg; John Michael Hasenkam, Aprilvej 8, DK-8210 Aarhus V; Lars Lyhne Knudsen, RudolfWulffsgade 6,4, DK-8000 Aarhus C, all of Denmark

[21] Appl. No.: 801,036

[22] Filed: Feb. 19, 1997

Related U.S. Application Data

[63] Continuation of Ser. No. 569,314, Dec. 8, 1995, abandoned, which is a continuation of Ser. No. 352,127, Dec. 1, 1994, abandoned, which is a division of Ser. No. 261,235, Jun. 14, 1994, Pat. No. 5,411,552, which is a continuation of Ser. No. 961,891, filed as PCT/DK91/00134 May 16, 1991 published as WO91/17720 Nov. 28, 1991, abandoned.

[30] Foreign Application Priority Data

May 18, 1990 [DK] Denmark ................................ 1246/90

[51] Int. Cl.$^6$ ...................................................... A61F 2/24
[52] U.S. Cl. .............................................. 623/2; 606/108
[58] Field of Search ........................ 623/2, 900; 606/108; 600/36

[56] References Cited

U.S. PATENT DOCUMENTS

| Re. 33,258 | 7/1990 | Onik . | |
|---|---|---|---|
| 3,409,013 | 11/1968 | Berry . | |
| 3,587,115 | 6/1971 | Shiley . | |
| 3,671,979 | 6/1972 | Moulopoulos | 623/2 |
| 3,755,823 | 9/1973 | Hancock . | |
| 4,056,854 | 11/1977 | Boretos et al. | 623/2 |
| 4,106,129 | 8/1978 | Carpentier et al. . | |
| 4,222,126 | 9/1980 | Boretos et al. . | |
| 4,574,803 | 3/1986 | Starz . | |
| 4,580,568 | 4/1986 | Gianturco . | |
| 4,592,340 | 6/1986 | Boyles | 623/2 |
| 4,612,011 | 9/1986 | Kautzky . | |

(List continued on next page.)

FOREIGN PATENT DOCUMENTS

| 0103546 | 3/1984 | European Pat. Off. | 623/2 |
|---|---|---|---|
| 0103546 A1 | 3/1984 | European Pat. Off. . | |
| 1258406 | 9/1986 | U.S.S.R. | 623/2 |
| 1271508 | 11/1986 | U.S.S.R. | 623/2 |
| 2056023 | 3/1981 | United Kingdom . | |
| 9117720 | 11/1991 | WIPO . | |
| 9217118 | 10/1992 | WIPO . | |

OTHER PUBLICATIONS

Sixteenth Edition of *The Merck Manual of Diagnosis and Therapy* (1992) "Valvular Heart Disease," p. 546–553.

Yamaguchi, Case Description, "A Case of a Reoperation using a Balloon Catheter with blocked Pars Ascendes Aortae," Kyobu Geka, Oct. 1989, 42:11, pp. 961–964.

World Medical Manufacturing Corporation, Talent Endovascular Bifurcated Spring Graft System Composite Design brochure, no date.

*Primary Examiner*—David H. Willse
*Attorney, Agent, or Firm*—Jeffry J. Grainger; Jens E. Hoekendijk; Michael J. Lynch

[57] ABSTRACT

A valve prosthesis (9) for implantation in the body by use of catheter (11) comprises a stent made from an expandable cylinder-shaped thread structure (2,3) comprising several spaced apices (4). The elastically collapsible valve (4) is mounted on the stent as the commissural points (5) of the valve (6) are secured to the projecting apices (4).

The valve prosthesis (9) can be compressed around the balloon means (13) of the balloon catheter (11) and be inserted in a channel, for instance in the aorta (10). When the valve prosthesis is placed correctly the balloon means (13) is inflated thereby expanding the stent and wedging it against the wall of aorta. The balloon means is provided with beads (14) to ensure a steady fastening of the valve prosthesis on the balloon means during insertion and expansion.

The valve prosthesis (9) and the balloon catheter (11) make it possible to insert a cardiac valve prosthesis without a surgical operation comprising opening the thoracic cavity.

8 Claims, 4 Drawing Sheets

U.S. PATENT DOCUMENTS

| | | |
|---|---|---|
| 4,631,052 | 12/1986 | Kensey . |
| 4,733,665 | 3/1988 | Palmaz ...................................... 606/108 |
| 4,777,951 | 10/1988 | Cribier et al. . |
| 4,787,899 | 11/1988 | Lazarus . |
| 4,787,901 | 11/1988 | Baykut . |
| 4,796,629 | 1/1989 | Grayzel . |
| 4,878,495 | 11/1989 | Grayzel . |
| 4,883,458 | 11/1989 | Shiber . |
| 4,966,604 | 10/1990 | Reiss . |
| 4,979,939 | 12/1990 | Shiber . |
| 4,986,830 | 1/1991 | Owens et al. . |
| 4,994,077 | 2/1991 | Dobben ...................................... 623/2 |
| 5,007,896 | 4/1991 | Shiber . |
| 5,011,488 | 4/1991 | Ginsburg . |
| 5,026,366 | 6/1991 | Leckrone . |
| 5,032,128 | 7/1991 | Alonso . |
| 5,047,041 | 9/1991 | Samuels . |
| 5,080,660 | 1/1992 | Buelna . |
| 5,089,015 | 2/1992 | Ross . |
| 5,152,771 | 10/1992 | Sabbaghian et al. . |
| 5,163,953 | 11/1992 | Vince . |
| 5,167,628 | 12/1992 | Boyles . |
| 5,295,958 | 3/1994 | Shturman . |
| 5,332,402 | 7/1994 | Teitelbaum . |
| 5,397,351 | 3/1995 | Pavcnik et al. . |
| 5,411,552 | 5/1995 | Andersen et al. . |
| 5,443,446 | 8/1995 | Shturman . |
| 5,480,424 | 1/1996 | Cox . |
| 5,545,209 | 8/1996 | Roberts et al. . |
| 5,593,405 | 1/1997 | Osypka . |

SYSTEM AND METHOD FOR IMPLANTING CARDIAC VALVES

This is a continuation of application Ser. No. 08/569,314, filed Dec. 8, 1995, now abandoned, which is a continuation of application Ser. No. 08/352,127, filed Dec. 1, 1994, now abandoned, which is a divisional of application Ser. No. 08/261,235, filed Jun. 14, 1994, now U.S. Pat. No. 5,411,552, which was continuation of application Ser. No. 07/961,891, filed as PCT/DK91/00134 May 16, 1991 published as WO91/17720 Nov. 28, 1991, now abandoned.

BACKGROUND OF THE INVENTION

The present invention relates to a valve prosthesis, preferably a cardiac valve prosthesis, for implantation in the body and comprising a collapsible elastic valve which is mounted on an elastic stent wherein the commissural points of the elastic collapsible valve are mounted on the cylinder surface of the elastic stent.

Valve prostheses of this type are usually implanted in one of the channels of the body to replace a natural valve. In the present description the invention will be explained in connection with a cardiac valve prosthesis for implantation in aorta. However, it will be possible to use a valve prosthesis according to the invention in connection with implantation in other channels in the body by using the same technique as the one used for implantation of cardiac valve prosthesis. Such an implantation may, e.g., comprise the implantation of:

1. a valve (for instance a cardiac valve) in the veins,
2. a valve in the esophagus and at the stomach,
3. a valve in the ureter and/or the vesica,
4. a valve in the biliary passages,
5. a valve in the lymphatic system, and
6. a valve in the intestines.

An existing natural valve in the body is traditionally replaced with a valve prosthesis by a surgical implantation. However, a surgical implantation is often an exacting operation. Thus, today the implantation of cardiac valves are solely made by surgical technique where the thoracic cavity is opened. The operation calls for the use of a heart and lung machine for external circulation of the blood as the heart is stopped and opened during the surgical intervention and the artificial cardiac valves are subsequently sewed in.

Due to its exacting character, it is impossible to offer such operation to certain people. For instance, this is due to the fact that the person is physically weak because of age or illness. Moreover, the number of heart and lung machines available at a hospital will be a substantially limiting factor.

Cardiac valve prostheses that need no surgical intervention are known as there are used for implantation by means of a technique of catheterization. Examples of such valve prostheses are described in U.S. Pat. Nos. 3,671,979 and 4,056,854. However, both of these valve prostheses are connected to means which lead to the surface of the patient either for a subsequent activation of the valve or for a subsequent reposition or removal of the valve prosthesis. With these valve prostheses it is impossible to make an implantation which makes it possible for the patient to resume a substantially normal life in the same way as it is possible in connection with a surgical implantation of a cardiac valve.

From U.S. Pat. No. 3,755,823 an elastic stent for a cardiac valve prosthesis is known. However, this valve prostheses is not designed for implantation in the body by catheterization. Even though this patent contains no detailed explanation, the description indicates that this valve prosthesis is designed for implantation and sewing on by a surgical intervention.

Moreover, from U.S. Pat. Nos. 4,856,516 and 4,733,665 different shapes of expandable stents are known. These stents are made to be expanded by impression of a radially outward force coming from a balloon catheter or the like. These stents are made to reinforce the wall when there is a risk that the channel is closed and/or compressed.

The nearest prior art may be that the described in GB-A-2,056,023. This document discloses an elastic stent as described by way of introduction. Thus, the stent described comprises an elastic collapsible valve mounted on the cylinder surface of a cylindrical stent. However, the valve prosthesis including the stent is designated for mounting through a surgical intervention. Even though the stent is slightly collapsible, it will not be suited for implantation by a catheterization procedure.

SUMMARY OF THE INVENTION

It is the object of the present invention to provide a valve prosthesis of the type mentioned in the introductory part, which permits implantation without surgical intervention in the body and by using a catheter technique known per se and which makes it possible for the patient to resume a substantially normal life.

This is achieved according to the invention with a valve prosthesis of the type mentioned in the introductory part, which is characterized in that the stent is made from a radially collapsible and re-expandable cylindrical support means for folding and expanding together with the collapsible valve for implantation in the body by means of a technique of catheterization.

The collapsible elastic valve is mounted on the stent for instance by gluing, welding or by means of a number of suitable sutures.

If the support means are made from a thread structure, this can for instance be grate shaped, loop shaped or helical. This makes it possible to compress the stent and the collapsible valve mounted thereon for placing on the insertion catheter. The use of a non-self-expandable stent may, e.g., be effected by a compression of the stent around the expansion arrangement of the catheter which preferably consists of a balloon. When using a self-expandable stent, a catheter with an expansion arrangement is not used. In this case the stent is compressed and is inserted into an insertion or protection cap from which the stent is eliminated after implantation in order to obtain an expansion due to the stresses in the compressed support means, which for instance may be made from plastics or metal. After the compression the entire outer dimension is relatively small, which makes it possible to introduce the valve prostheses through a channel in the body.

When the valve prosthesis is introduced and placed correctly, the stent is expanded by self-expansion or by means of the expansion arrangement until the stent is given an outer dimension which is slightly larger than the channel in which it is placed. As the stent is elastic, a contraction of the stent is prevented once it is expanded. The stiffness in the material of the support means contributes to maintain the expanded shape of the stent. After the expansion is made, the expansion arrangement of the catheter is contracted and the catheter can be removed from the channel. The inlet opening can subsequently be closed and the patient will then be able to resume a normal life.

The valve prosthesis according to the invention does not require an actual operation but merely a small intervention to optionally expose the body channel, e.g., a vein, through which the insertion takes place. Thus, patients for whom an operation would be associated with high risk can be offered implantation of, for instance, cardiac valves. After the implantation has taken place, the after-treatment will advantageously be shorter than normal, which means fewer hospital days for the patient. Moreover, it is assumed that it will be possible to implant the valve prosthesis under local anaesthetic.

The valve prosthesis can be used to replace a natural valve or to establish a new valve function in one of the channels in the body which do not naturally contain a valve. For instance this goes for veins (arteries and veins) on a place without natural valves. The function of the valve prosthesis is then to ensure that the blood flows in one direction only. The valve is meant to be used in veins in the legs of persons suffering from varicose veins (varices).

In persons having varicose veins the blood flows in a wrong direction, viz. from the central veins in the center of the leg towards the superficial veins. Among other things, this is due to the changed pressure in the legs, upright working position and other conditions. A valve prosthesis according to the invention may easily be placed in the veins and prevent the flow of the blood in a wrong direction.

Also, the valve prosthesis can be used in connection with diseases, for instance cancerous tumors, where too much humour is produced. If the humour is able to flow from the cancerous tumor through several channels, it is possible to drain the humour in one desired direction through the channels of the body by an appropriate placing of the valve prosthesis.

When the valve prosthesis is used as a cardiac valve prosthesis in the aorta, it is possible to mount it in three positions, viz., in the descending part of the aorta in a position between the coronary arteries and the left ventricle of the heart, or in the aorta in a position immediately after the mouth of the coronary arteries.

The cardiac valve prosthesis can also be used in other places than in the aorta. Thus, the valve prosthesis can be used in the pulmonary artery and/or the right ventricle of the heart for replacing the pulmonary valves. Likewise, the cardiac valve prosthesis can be used in the passage between the right auricle of the heart and the right ventricle of the heart (tricuspidalostium) and the passage between the left auricle of the heart and the left ventricle of the heart (mistralostium) for replacing the tricuspidal valve and the mitral valve, respectively.

Even though the cardiac valve preferably is meant to be used for patients suffering from aorta insufficiency and who cannot be offered an open heart surgery, the valve prosthesis can also be used for patents in connection with treatment of aorta stenosis. Several of the patients with aorta stenosis are elderly people who cannot be offered a surgical cardiac operation. The patients are offered balloon dilatation of the aorta stenosis which may result in an aorta insufficiency as a side effect of the treatment.

As to these patients it is possible to insert a valve prosthesis in the descending or ascending part of the aorta thoracalis a few days or weeks before the balloon dilatation. As a result thereof, the left ventricle is protected against weight if the subsequent balloon dilatation of the stenosis results in aorta insufficiency. In certain cases the weight (reflux) on the left ventricle is reduced by up to approximately 75%.

Furthermore, the stent may be made with a relatively great height and with a cylinder surface which is closed by a suitable material. Thus, a vascular prosthesis known per se is formed wherein the valve is mounted. This may facilitate the implantation of the valve prosthesis, for instance in the arcus aorta. Moreover, the great surface which abuts the inner wall of the channel contributes to ensure the securing of the valve prosthesis in the channel. This embodiment is also suitable as valve prosthesis which is inserted in veins. As veins have relatively thin and weaker walls than arteries, it is desirable that the valve prosthesis has a greater surface to distribute the outward pressure which is necessary to secure the valve prosthesis.

Moreover, the invention relates to a balloon catheter for implanting a valve prosthesis according to the invention and comprising a channel for injection of a fluid for the inflation of the balloon means of the catheter and an insertion cap wherein the balloon means of the catheter and a collapsible valve prosthesis mounted thereon are located during the injection, characterized in that the balloon means are provided with profiled surface which is made to ensure a steady fastening of the valve prosthesis during the withdrawal of the balloon means from the protection cap and the subsequent inflation for the expansion of the stent.

Different balloon catheters for implanting cores in the body are known. For instance, such balloon catheters are known from U.S. Pat. Nos. 4,856,516, 4,733,665 and 4,796,629 and from DE publication No. 2,246,526. However, the known balloon catheters have a smooth, or a slightly wavy surface. The use of such balloon catheter is disadvantageous for mounting a valve prosthesis in a channel having a large flow as for instance the aorta. A large humour flow is able to displace the stent on the smooth surface of the balloon and makes an accurate positioning difficult. This drawback has been remedied with the balloon catheter according to the present invention as the profiled surface prevents a displacement of the valve prosthesis in relation to the balloon means during introduction and the subsequent inflation of the balloon means.

In connection with the implantation, any prior art technique may be used to supervise an accurate introduction and positioning of the valve prosthesis. Thus, guide wires for the catheter, X-ray supervision, injection of X-ray traceable liquids, ultrasonic measuring, etc. may be used.

DESCRIPTION OF THE DRAWINGS

The invention will now be explained in detail with reference to the accompanying schematical drawing, wherein.

DETAILED DESCRIPTION OF THE PREFERRED EMBODIMENTS

Figure 1:
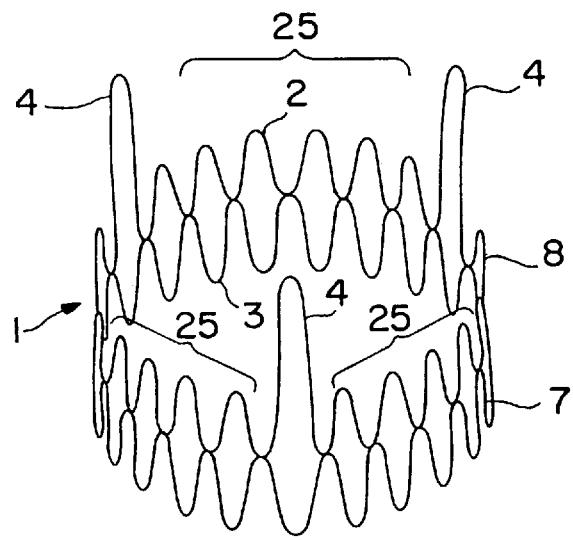
FIG. 1 shows a perspective view of a stent without a valve.
Figure 2:
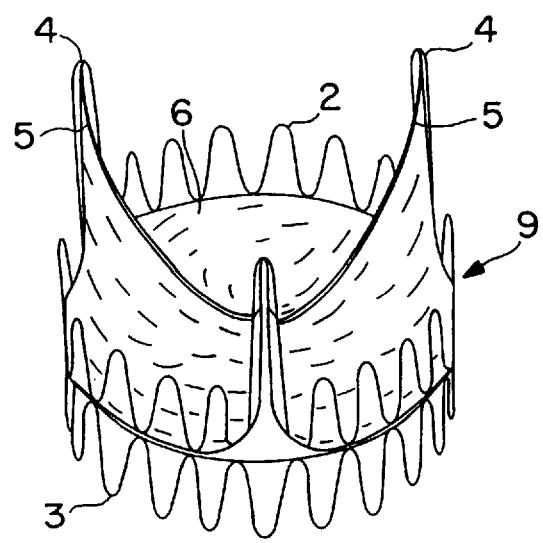
FIG. 2 is a perspective view of a valve prosthesis according to the invention made from the stent shown in FIG. 1 having a biological valve mounted thereon.

FIG. 1 shows a stent 1 made by support means in the form of two 0.55 mm surgical stainless steel wires 2,3. The wires are folded in 15 loops. Three loops 4 are 14 mm in height and are intended to secure the commissural points 5 (see FIG. 2) from a biological cardiac valve 6 which is mounted in the stent 1. The remaining loops have a height of 8 mm. These loops form circumferentially expandable sections 25 between the commissural points 5 forming commissural supports. Each of the two folded wires 2,3 is bent to form rings 7,8 which are closed by welding the ends. The two rings are placed on top of each other as will appear from FIG. 1 and they are mutually secured by means of a number of sutures (not shown). The lower ring is circumferentially expandable at least along sections thereof which correspond to the circumferentially expandable sections 25. By using a substantially cylindrical thread structure projecting apices, a reduction in weight is obtained as compared to a stent which is exclusively cylindrical with the same loop heights for all the loops.

The biological valve 6 was removed from a slaughtered pig of 100 kg. The valve was cleaned before mounting in the stent 1. The cleaned valve has an outer diameter of 25–27 mm and the height of the three commissural points 5 is 8 mm. The valve 6 is mounted in the stent by means of a suitable number of sutures to form the cardiac valve prosthesis 9 shown in FIG. 2. The valve prosthesis produced is used for performing tests in pigs by implantation of cardiac valve prosthesis. However, the cardiac valve prosthesis for use in human beings has a corresponding form.

Figure 3:
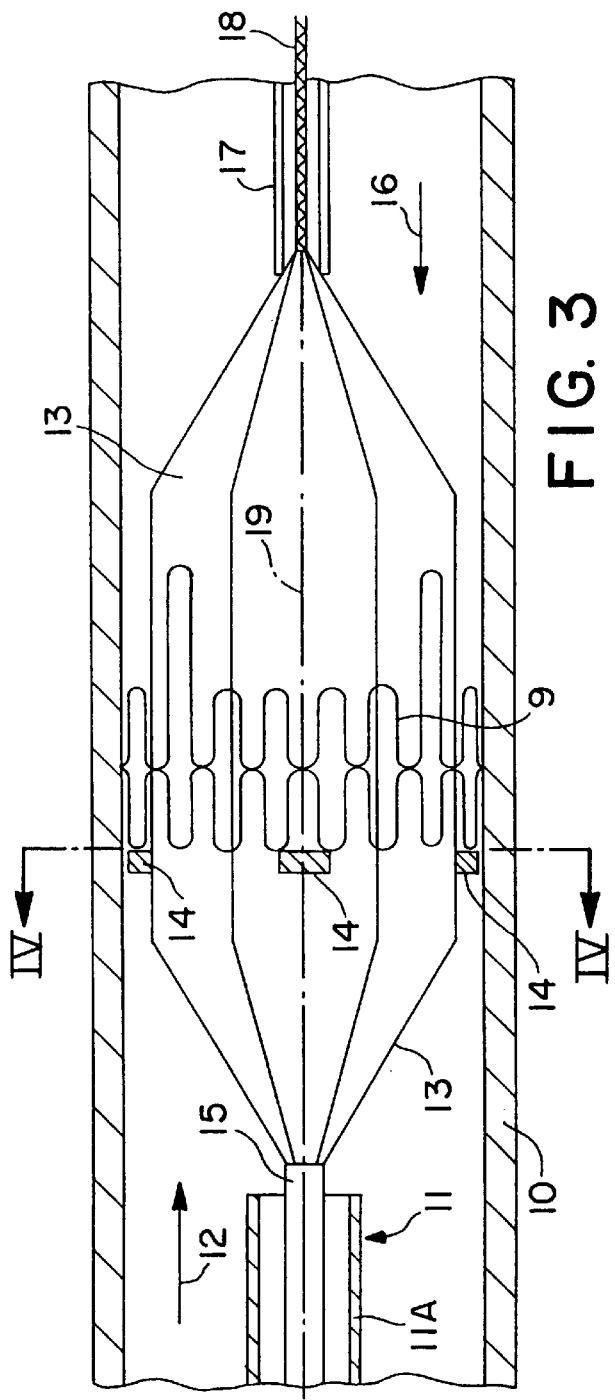
FIG. 3 is a partial view through the aorta illustrating a partially inflated balloon catheter.

FIG. 3 shows a partial view through the aorta 10. A balloon catheter 11 is introduced in the aorta according to the direction of an arrow 12. In the Figure shown the balloon means 13 of the balloon catheter is led out of the protection cap 11A and is partly inflated through a fluid channel 15, which is led to the surface of the patient. The balloon means 13 constitutes a tri-sectional balloon upon which the cardiac valve prosthesis is placed. In the form shown, the cardiac valve prosthesis is expanded exactly to be in contact with the aorta 10. The balloon means 13 is provided with three projecting beads 14 which are engaged with the one side of the cardiac valve prosthesis 9. The blood flowing through the aorta according to the direction of an arrow 16 will thus cause the cardiac valve prosthesis 9 to abut on the beads 14 and the valve cannot be displaced in relation to the balloon means 13. Moreover, the balloon catheter used comprises a central channel 17 to receive a guide wire 18 which is used in a way known per se for supervising the introduction of the catheter through fluoroscopi. In the shown embodiment beads 14 are only used at one side of the valve prosthesis, but, however, it will often be desirable to use the beads in pairs placed along lines parallel to the longitudinal axes 19 through the balloon means 13. In this case the spacing of the pair of beads 14 will correspond to the height of the loops of the stent. This makes it possible to make an effective fastening of a valve prosthesis on balloon means. Moreover, the fastening on the balloon means may be provided by using balloon means with an indentation in the surface (not shown).

Figure 4:
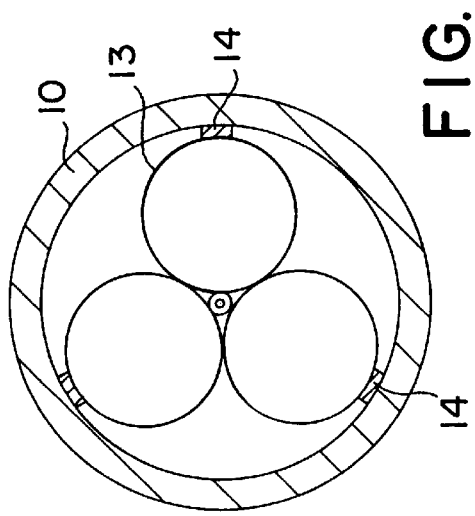
FIG. 4 is a cross section through the embodiment shown in FIG. 9, FIGS. 5–7 are views illustrating the introduction and implantation of a valve prosthesis of the invention in the aorta.

FIG. 4 shows a cross section through the embodiment shown in FIG. 3 illustrating the placing of the beads 14 on the tri-sectional balloon means 13.

A balloon catheter of the above-described type which was used in tests of implanting of cardiac valve prosthesis 9 in pigs had the following dimensions. Each of the three balloons was 60 mm in length and 15 mm in diameter. The total diameter for the three inflated balloons was 31 mm and in the balloon catheter used two beads 14 having a height of 3 mm were mounted on each side of the three balloons. The beads had a spacing of 15 mm. The protection cap 11A of the balloon catheter had an outer diameter of 13.6 mm and an inner diameter of 12.5 mm and a length of 75 cm. The balloon catheter was provided with a standard guide wire having a diameter of 0.9 mm and a length 300 cm.

Figure 5:
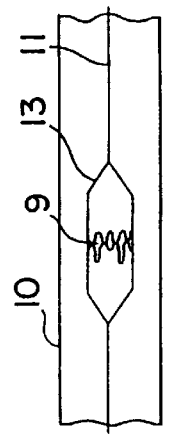
Figure 6:
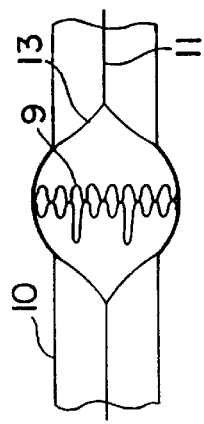
Figure 7:
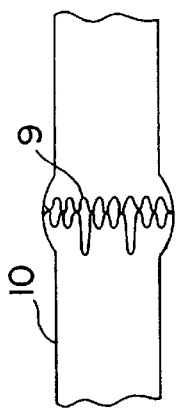

FIGS. 5–7 show the valve prosthesis 9 at different steps in introducing and implanting in the aorta 10 by means of the catheter 11 having the inflatable balloon means 13. The cardiac valve prosthesis 9 is initially placed above the deflated balloon means 13 and compressed manually around the balloon means (FIG. 5), whereafter the outer diameter for the valve prosthesis is approximately 10 mm. After the introduction and positioning, the balloon means 13 is inflated (FIG. 6), thereby contributing an outer dimension of approximately 30 mm to the cardiac valve prosthesis. To obtain an effective fastening in the aorta, the outer dimension of the cardiac valve prosthesis is greater than the diameter of the aorta. This means that the prosthesis is tight against the inner wall of the aorta with a pressure which is sufficiently large to counteract a detachment due to the flow of the blood. The balloon catheter 11 may subsequently be removed from the aorta 10 (FIG. 7). Due to the stiffness of the metal the valve prosthesis will prevent a contraction. However, smaller contractions may occur (<10% diameter reduction) after the deflation and removal of the balloon catheter 13. When the valve prosthesis is mounted as shown in FIG. 7, the patient will be able to resume a substantially normal life after a few days.

Figure 8:
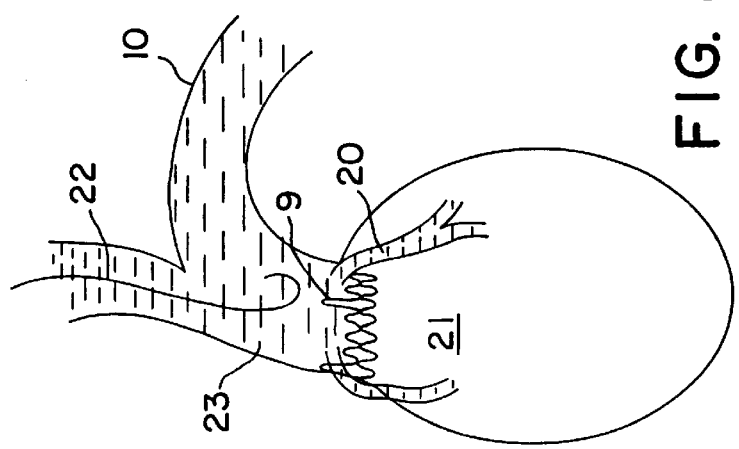
FIGS. 8–10 are views illustrating three possible positions of a cardiac valve prosthesis.
Figure 9:
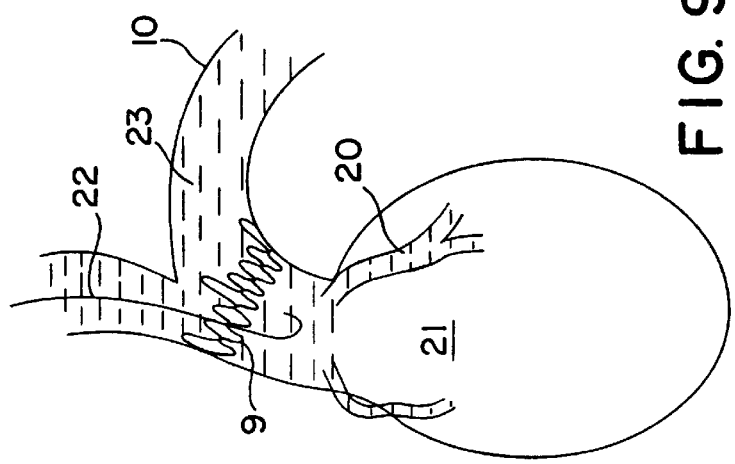
Figure 10:
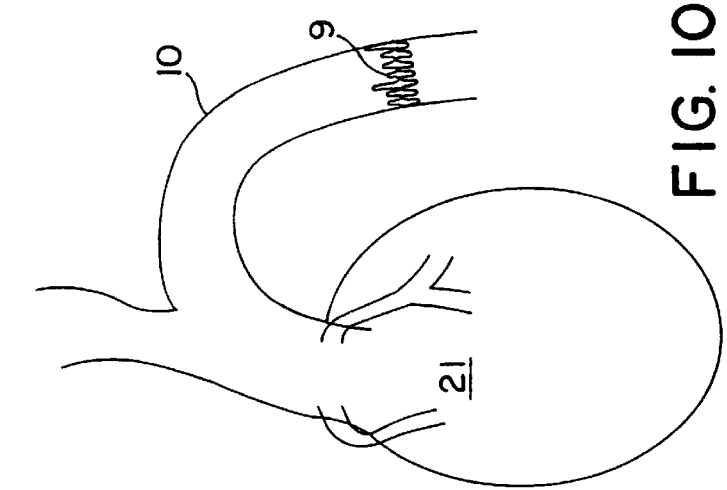

FIGS. 8–10 show the positioning of the valve prosthesis 9 as cardiac valve prosthesis in the aorta 10 in three different positions, i.e., in a position between the coronary arteries 20 and the left ventricle of the heart 21 (FIG. 8), in a position immediately after the mouth of the coronary arteries in the ascending part of the aorta (FIG. 9), and in a position in the descending part of the aorta 10. The positioning of the valve prosthesis is chosen in accordance with the diagnosis of the illness of the patient. By placing the cardiac valve prosthesis as shown in FIG. 8, there is a risk of detachment and/or covering the mouth of the coronary arteries, and therefore it is preferred to use a higher stent which, for instance, comprises several ranges placed on top of each other. This allows a fixation of the prosthesis at a place after the mouth of coronary arteries even though the valve itself is in the position between the coronary arteries and the left ventricle. FIGS. 8 and 9 show how a contrast medium 23 is injected by means of a so-called pigtail catheter for registration of tightness of the implanted valve prosthesis 9.

A specific embodiment for a valve prosthesis and a balloon catheter for implanting the valve prosthesis has been explained above. However, it is obvious that it is possible to modify the valve prosthesis depending on the desired use, and moreover, it is possible to modify the catheter used in the implantation. Thus, the stent of the valve prosthesis may be made solely of one closed ring folded in a number of loops or with three or more mutually secured loop-shaped rings placed on top of each other. Moreover, it is possible to make the stent having a thread structure which instead of loops is grate shaped, helical or is formed otherwise if only it is ensured that the form of the stent permits the compression and expansion of the stent and fastening of the collapsible valve. Instead of a biological valve it might be possible to use other collapsible valves, such as valves made from synthetic materials, e.g., polyurethane. It is also possible to use valves with more or fewer flaps than three.

Figure 11:
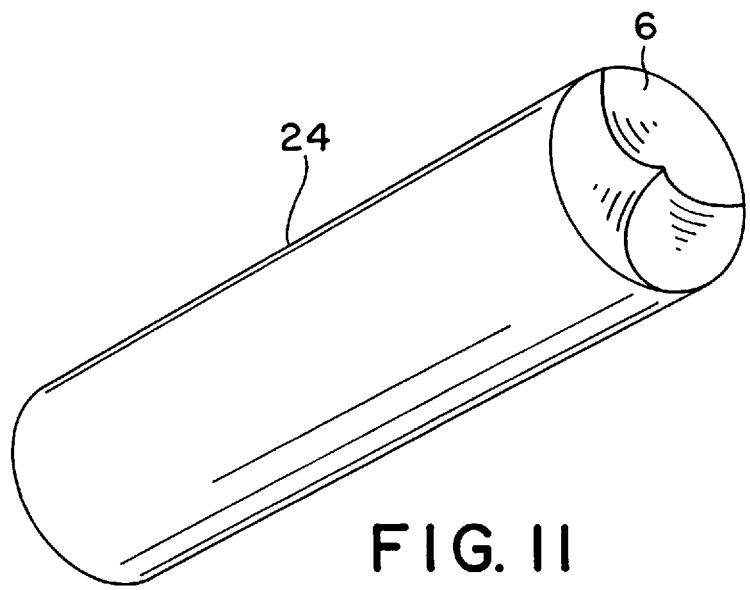
FIGS. 11–12 are perspective views illustrating two further embodiments of a valve prosthesis having a closed cylindrical wall.
Figure 12:
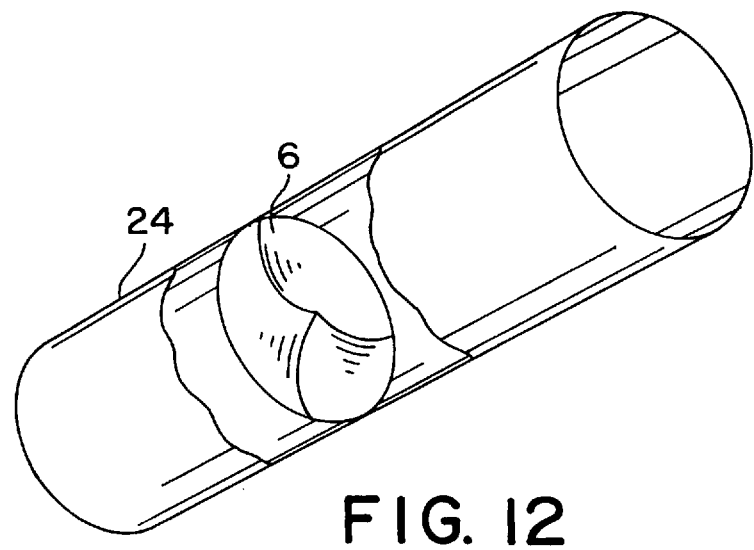

It is possible to make the valve prosthesis with a closed cylinder surface as illustrated in FIGS. 11 and 12. In both Figures the support means of the valve prosthesis is made of an elongated tubular means 24 having a closed cylinder surface. This valve prosthesis is intended to expand by self-expansion or by means of a catheter according to the invention. This prosthesis is especially suitable for placing in veins and other channels where only a small pressure is exerted against the wall of the channel. In FIG. 11 the valve 6 is mounted at the end of the tubular means 24. In FIG. 12 an embodiment is shown where the valve 6 is mounted in a central position in the tubular means 24.

An explanation of a method of implanting a valve prosthesis according to the invention is given below:

- a valve prosthesis 9 made of a stent 1 and a collapsible valve 6, as described above, is placed on a deflated balloon means and is manually compressed thereon,
- the balloon means 13 and the valve prosthesis are drawn into an insertion cover 11A,
- a guide wire 18 is inserted into the left ventricle of the heart through the central opening 17 of the balloon catheter under continuous fluoroscopi,
- the insertion cover 11A conveys the guide wire 18 to a point in the channel in the immediate vicinity of the desired position of the valve prosthesis,
- the balloon means 13 is pushed out of the protection cap 11A and the valve prosthesis is positioned in the desired position if necessary by use of further registration means to ensure an accurate positioning,
- the balloon means 13 is inflated with a certain overstretching of the channel,
- the balloon means 13 is deflated, and
- the balloon means 13, the guide wire 18 and the protection cap 11A are drawn out and the opening in the channel, if any, wherein the valve prosthesis is inserted can be closed.

We claim:

1. A system for implanting a valve in a body channel having an inner wall, the system comprising:
    a radially collapsible and expandable cylindrical stent;
    a radially collapsible and expandable valve mounted to the stent; and
    a catheter for introducing and securing the valve in the body channel, the catheter comprising an expandable member about which the cylindrical stent may be positioned together with the valve, fastening means on the expandable member on which the stent may be mounted to the expandable member, and a channel extending through the catheter for injecting a fluid into the expandable member so as to expand the expandable member from a collapsed profile suitable for introduction into the body channel to an expanded profile in which the stent engages the inner wall of the body channel so as to secure the valve therein.

2. A system as in claim 1 wherein the expandable member comprises a balloon.

3. A system as in claim 2 wherein the fastening means comprises a plurality of beads on the surface of the balloon.

4. A system as in claim 1 wherein the valve comprises a trilobate valve having a plurality of commissural points.

5. A system as in claim 4 wherein the stent comprises a plurality of circumferentially spaced apices for supporting the commissural points of the valve.

6. A system as in claim 5 wherein the stent comprises at least one wire bent so as to form a plurality of circumferentially spaced loops, a first portion of the loops comprising the apices for supporting the commissural points of the valve, and a second portion of the loops lying between the apices to allow the stent to radially expand and collapse.

7. A method of implanting a valve in a body channel having a wall, the method comprising:
    introducing a catheter into the body channel, the catheter including an expandable member near a distal end thereof, a fluid channel in communication with the expandable member, and a cylindrical stent mounted to the expandable member, the valve being mounted to the cylindrical stent, wherein the expandable member, the stent and the valve are in a collapsed configuration during said introducing;
    advancing the catheter within the body channel to a position wherein the valve is to be implanted; and
    radially expanding the expandable member together with the cylindrical stent and the valve by injecting a fluid through the fluid channel such that the stent engages the wall of the body channel so as to be secured therein.

8. The method of claim 7 wherein the step of radially expanding comprises inflating a balloon on the catheter with the fluid delivered through the fluid channel, the cylindrical stent being disposed about the balloon so as to expand therewith.

* * * * *